United States Patent
Burton et al.

(10) Patent No.: US 7,857,786 B2
(45) Date of Patent: Dec. 28, 2010

(54) BALLOON CATHETER HAVING IMPROVED BALLOON FOLDING CAPABILITY

(75) Inventors: David G. Burton, Bloomington, IN (US); David A. Drewes, Jr., Bloomington, IN (US); Eric R. Hennessy, Bloomington, IN (US); Darin G. Schaeffer, Bloomington, IN (US)

(73) Assignees: Cook Incorporated, Bloomington, IN (US); Sabin Corporation, Bloomington, IN (US)

( * ) Notice: Subject to any disclaimer, the term of this patent is extended or adjusted under 35 U.S.C. 154(b) by 185 days.

(21) Appl. No.: 11/926,767

(22) Filed: Oct. 29, 2007

(65) Prior Publication Data

US 2008/0132836 A1 Jun. 5, 2008

Related U.S. Application Data

(60) Provisional application No. 60/856,675, filed on Nov. 3, 2006, provisional application No. 60/861,198, filed on Nov. 27, 2006.

(51) Int. Cl.
*A61M 31/00* (2006.01)
(52) U.S. Cl. .................................. 604/103.14
(58) Field of Classification Search ............ 604/103.08, 604/103.14, 105, 103.06, 99.01, 103.07
See application file for complete search history.

(56) References Cited

U.S. PATENT DOCUMENTS

| | | | |
|---|---|---|---|
| 4,932,956 A | 6/1990 | Reddy et al. | |
| 4,976,690 A | 12/1990 | Solar et al. | |
| 5,041,125 A * | 8/1991 | Montano, Jr. | 606/192 |
| 5,254,091 A | 10/1993 | Aliahmad et al. | |
| 5,267,959 A | 12/1993 | Forman | |
| 5,295,994 A | 3/1994 | Bonutti | |
| 5,306,246 A | 4/1994 | Sahatjian et al. | |
| 5,496,271 A | 3/1996 | Burton et al. | |
| 5,733,301 A | 3/1998 | Forman | |
| 5,826,588 A | 10/1998 | Forman | |
| 5,876,376 A | 3/1999 | Schwab et al. | |
| 6,030,371 A | 2/2000 | Pursley | |
| 6,425,882 B1 | 7/2002 | Vigil | |
| 6,440,503 B1 | 8/2002 | Merdan et al. | |

(Continued)

FOREIGN PATENT DOCUMENTS

JP 2002-301160 10/2002

(Continued)

*Primary Examiner*—Nicholas D Lucchesi
*Assistant Examiner*—Pritesh Patel
(74) *Attorney, Agent, or Firm*—Brinks Hofer Gilson & Lione (57) ABSTRACT

The present invention provides apparatus and methods for facilitating folding of a balloon before, during or after a medical procedure. In a first embodiment, the apparatus generally comprises at least one catheter shaft member, a balloon disposed on a distal region of the catheter shaft member, and at least one folding member disposed along at least a proximal region of the balloon. The folding member may comprise at least one radially-outward projecting member integrally formed with or attached to the balloon, or an internally-formed groove in the balloon, which is adapted to promote twisting of the balloon to reduce the profile of the balloon in the deflated state. Optionally, biasing members may be disposed between the folding member and an adjacent portion of the balloon to promote folding of the balloon in a clockwise or counter-clockwise direction.

14 Claims, 6 Drawing Sheets

U.S. PATENT DOCUMENTS

| | | |
|---|---|---|
| 6,746,424 B2 | 6/2004 | Stamberg |
| 6,858,104 B2 | 2/2005 | Flanagan |
| 6,893,456 B2 | 5/2005 | Lumauig |
| 6,970,734 B2 | 11/2005 | Eidenschink et al. |
| 2004/0086674 A1 | 5/2004 | Holman |
| 2005/0113749 A1 | 5/2005 | Parsonage et al. |
| 2005/0197668 A1 | 9/2005 | Lim et al. |
| 2005/0211679 A1 | 9/2005 | Chiu et al. |

FOREIGN PATENT DOCUMENTS

| | | |
|---|---|---|
| WO | WO2005/113049 | 12/2005 |

* cited by examiner

BALLOON CATHETER HAVING IMPROVED BALLOON FOLDING CAPABILITY

PRIORITY CLAIM

This invention claims the benefit of priority of U.S. Provisional Application Ser. No. 60/856,675, entitled "Balloon Catheter Having Improved Balloon Folding Capability," filed Nov. 3, 2006, the disclosure of which is hereby incorporated by reference in its entirety, and further claims the benefit of priority of U.S. Provisional Application Ser. No. 60/861,198, entitled "Balloon Catheter Having Improved Balloon Folding Capability," filed Nov. 27, 2006, the disclosure of which is hereby incorporated by reference in its entirety.

BACKGROUND

The present invention relates generally to apparatus and methods for treating vascular conditions, and more specifically, to a balloon catheter having a configuration that improves the folding capability of a balloon after deflation of the balloon.

Atherosclerosis and other occlusive diseases are prevalent among a significant portion of the population. In such diseases, atherosclerotic plaque forms within the walls of the vessel and blocks or restricts blood flow through the vessel. Atherosclerosis commonly affects the coronary arteries, the aorta, the iliofemoral arteries and the carotid arteries. Several serious conditions may result from the restricted blood flow, such as ischemic events.

Various procedures are known for treating stenoses in the arterial vasculature, such as balloon angioplasty. During a balloon angioplasty procedure, a catheter having a deflated balloon attached thereto is inserted into a patient's vessel. In some cases, it is desirable to introduce the balloon in a configuration whereby the balloon is twisted or folded upon itself in order to reduce the radial profile of the balloon during delivery. Once positioned across a constricting lesion, the balloon is then inflated to widen the lumen to partially or fully restore patency to the vessel. After satisfactory widening of the stenosis has been achieved, the balloon is deflated. The catheter is then retracted and removed from the patient's vessel with the balloon in the deflated state.

An important problem that exists with the use of conventional angioplasty balloons is that they may not be reliably collapsed after deflation. For example, after the balloon is expanded to engage the vessel wall and then deflated, the balloon may obtain a flattened configuration, e.g., having two opposing regions that extend radially outward. In those cases, it may become difficult to withdraw the balloon from the patient's vessel. If an introducer sheath is used, the balloon may become caught within the sheath upon retraction and removal.

In view of the foregoing, there is a need for a balloon catheter that achieves a sufficiently collapsed radial profile in order to be removed after deflation. In particular, there is a need for an apparatus that promotes an orderly folding of the balloon upon itself, thereby achieving a reduced profile and reducing the likelihood that the balloon will become caught upon removal from the patient's vessel.

SUMMARY

The present invention provides apparatus and methods for treating a vascular condition, such as a stenosis formed within a vessel. The apparatus generally comprises at least one catheter shaft member, a balloon disposed on a distal region of the catheter shaft member, and at least one folding member disposed along at least a proximal region of the balloon. The folding member is adapted to promote twisting of the balloon to reduce the profile of the balloon in the deflated state, e.g., after an angioplasty procedure has been performed.

In a first embodiment, the balloon has a proximal taper, a distal taper, and a central region formed therebetween. At least one folding member is disposed along at least a portion of the proximal taper of the balloon. The folding member terminates proximal to the central region of the balloon, and therefore does not substantially interfere with the treatment of the vascular condition by the balloon.

The folding member may comprise at least one radially-projecting member that is integrally formed with the balloon or attached thereto. If a radially-projecting member is employed, the folding member may comprise a proximal tapered portion, a tapered central portion extending between proximal and distal ends, or a fluted configuration. Optionally, the folding member may comprise a spiral shape wherein the folding member has proximal and distal ends that are circumferentially offset from one another to facilitate folding of the balloon. In an alternative embodiment, the folding member may comprise at least one internal groove formed integrally with the balloon, preferably having an inverted fluted configuration.

In another embodiment, at least one biasing member is disposed between the folding member and an adjacent portion of the balloon. The biasing member may comprise a bond, for example, which heat-bonds to the folding member to the balloon. Alternatively, the biasing member may comprise a bonding substance, such as a biocompatible glue or other suitable adhesive. The biasing member may be coupled to a respective folding member at a location clockwise to each folding member to promote folding of the balloon in a clockwise direction, or vice versa.

In an exemplary method of operation, the balloon catheter is delivered into a patient's vessel with the balloon in a deflated state, whereby the balloon is folded over itself in a clockwise or counter-clockwise fashion to reduce its radial profile. When positioned at a desired location, inflation fluid is provided to inflate the balloon, thereby expanding the balloon and at least one folding member. A vascular condition, such as a stenosis, then may be treated using the central region of the balloon. Since the folding members do not overlap with the central region, they do not substantially interfere with the treatment of the vascular condition.

When the vascular condition has been satisfactorily treated, the balloon is deflated. The balloon catheter then may be retracted proximally into the confines of an outer sheath, whereby the configuration of the folding members, and optionally the biasing members, causes the balloon to contract and fold in a more orderly, clockwise or counter-clockwise fashion, thereby reducing the cross-sectional profile of the balloon in the deflated state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention.

Moreover, in the figures, like referenced numerals designate corresponding parts throughout the different views.

FIGS. 2A-2B are, respectively, a side-elevational view of a second embodiment and a side view of the apparatus of FIG. 2A.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure.

Figure 1A:
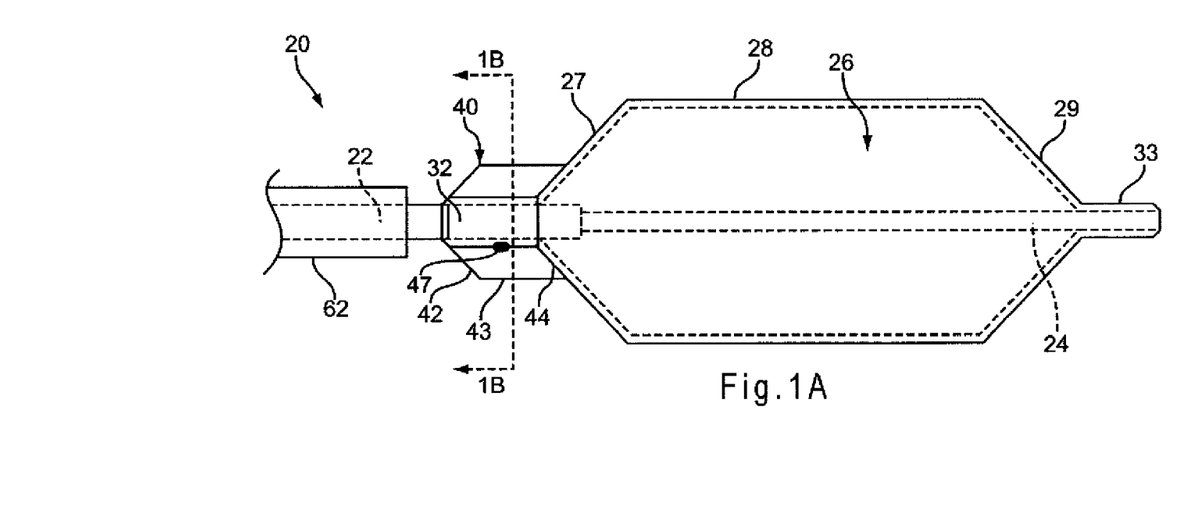
FIGS. 1A-1B are, respectively, a side-elevational view of a first embodiment and a cross-sectional view along line 1B-1B of FIG. 1A.
Figure 1B:
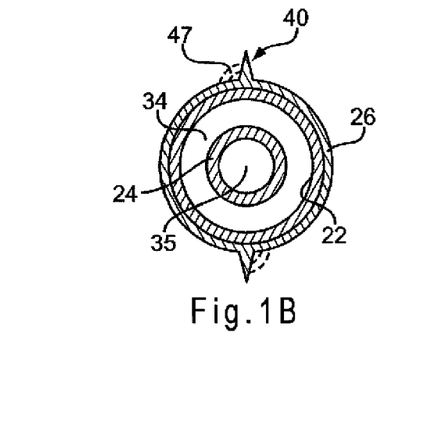

Referring now to FIGS. 1A-1B, a first embodiment of a balloon catheter having an improved balloon folding capability is described. In FIG. 1A, balloon catheter 20 comprises balloon 26, along with at least one catheter shaft member. In the embodiments depicted herein, the catheter shaft member comprises outer and inner shaft members 22 and 24. However, it will be apparent that one integrally-formed catheter shaft member may be employed, or alternatively, greater than two shaft members may be employed.

Outer shaft member 22 and inner shaft member 24 preferably comprise flexible, tubular members that may be formed from one or more semi-rigid polymers. For example, the shaft members may be manufactured from polyurethane, polyethylene, polytetrafluoroethylene, fluorinated ethylene propylene, polyamides or polyesters, or alternatively, tetrafluoroethylene or the like.

Balloon 26, which has proximal attachment region 32 and distal attachment region 33, may be manufactured from any suitable balloon material used during an interventional procedure, such as an angioplasty procedure. Proximal attachment region 32 of balloon 26 is attached to an exterior surface of outer shaft member 22, while distal attachment region 32 is attached to an exterior surface of inner shaft member 24, which extends distal to outer shaft member 22, as shown in FIG. 1A. Proximal and distal attachment regions 32 and 33 of balloon 26 may be affixed to the exterior surfaces of outer and inner shaft members 22 and 24, respectively, using an adhesive, such a biocompatible glue, or alternatively, using a heat-bond, heat-shrink tubing, one or more tie-down bands, or the like.

Outer and inner shaft members 22 and 24 preferably are configured such that an outer diameter of inner shaft member 24 is smaller than an inner diameter of outer shaft member 22, thereby creating a cavity forming inflation lumen 34, as shown in FIG. 1B. The distal end of outer shaft member 22 may terminate within the confines of balloon 26, as shown in FIG. 1A, such that inflation fluid delivered via inflation lumen 34 is channeled into the confines of balloon 26 to achieve inflation.

Further, inner shaft member 24 preferably comprises a hollow tubular member having inner lumen 35 formed therein, as shown in FIG. 1B. Inner lumen 35 spans from a proximal end to a distal end of inner shaft member 24 and is configured to receive a wire guide and/or other medical components. In one exemplary method of use, a wire guide may be delivered percutaneously to a site of a vascular condition, and balloon catheter 20 may be delivered over the wire guide by placing the distal end of inner shaft member 24 over the wire guide and advancing balloon catheter 20 distally while balloon 26 is in a deflated state.

Balloon 26 may comprise any number of configurations. In the embodiments shown herein, balloon 26 comprises proximal taper 27, distal taper 29, and central region 28 formed therebetween, as shown in FIG. 1A. Central region 28 may be sized and configured to perform angioplasty on an inner wall of a blood vessel. Alternatively, balloon 26 may have proximal and distal regions and comprise other shapes, for example, a substantially circular shape, oval shape, or the like.

In accordance with one aspect, balloon catheter 20 further comprises at least one folding member 40, which may be attached to or integrally formed with balloon 26. In the embodiment of FIGS. 1A-1B, at least one folding member 40 comprises a radially-projecting member that preferably is generally wing-shaped or tab-shaped. In this embodiment, two folding members 40 are provided and are spaced apart approximately 180 degrees from each other around the circumference of proximal attachment region 32. It will be apparent that while two folding members 40 are depicted, greater or fewer may be employed.

Folding members 40 preferably comprise tapered proximal region 42, tapered distal region 44, and central region 43 disposed therebetween. If folding members 40 are integrally formed with balloon 26, then proximal taper 27 of balloon 26 may be molded to transition into central region 43, as shown in FIG. 1A. If manufactured separately, tapered distal region 44 of folding member 40 may be attached to proximal taper 27 of balloon 26, e.g., via adhesive or other suitable means.

As shown in FIG. 1A, folding members 40 are disposed along at least a portion of proximal taper 27, and further are disposed partially along proximal attachment region 32, which is attached to outer shaft member 22. Alternatively, folding members 40 may be disposed completely on proximal taper 27, or completely on proximal attachment region 32. However, in accordance with one aspect, folding members 40 are not disposed along central region 28 of balloon 26, so that the folding members do not substantially interfere with treatment of a vascular condition by central region 28.

One or more folding members 40 may be coupled to the adjacent balloon material using a biasing member 47. Biasing member 47 may comprise a heat-bond between folding member 40 and the adjacent balloon material, or alternatively, may comprise a bonding substance, for example, a biocompatible glue or adhesive, that is disposed between folding members 40 and an adjacent portion of balloon 26, as shown in FIG. 1B.

The presence of biasing member 47 develops a pretwisted capability that is adapted to facilitate folding of balloon 26 in a more orderly fashion. For example, in the embodiment of FIGS. 1A-1B, one biasing member 47 is coupled to a respective folding member 40 at a location counter-clockwise to the folding member. As explained below, this configuration forms a pretwist in balloon 26 that causes folding of the balloon in a counter-clockwise direction. Alternatively, biasing member 47 may be coupled to a respective folding member 40 at a location clockwise to the folding member to promote folding in a clockwise direction.

It should be noted that folding members 40 may comprise a tapered or pointed configuration when viewed from a cross-sectional profile, as shown in FIG. 1B. Alternatively, folding members 40 may comprise a substantially rectangular cross-sectional profile, for example, as illustrated by folding members 140, as shown in FIG. 2B, below.

In an exemplary method of operation, balloon catheter 20 is delivered into a patient's vessel with balloon 26 in a deflated state, whereby balloon 26 is folded over itself in a counter-clockwise fashion to reduce its radial profile. Folding members 40 are also folded in a counter-clockwise direction over proximal attachment region 32 and/or proximal taper 27 of balloon 26 in the contracted delivery state. When positioned at a desired location, inflation fluid is provided by inflation lumen 34 to inflate balloon 26, thereby expanding balloon 26 and folding members 40, as depicted in FIGS. 1A-1B. A vascular condition, such as a stenosis, then may be treated using central region 28 of balloon 26. Advantageously, folding members 40 do not overlap with central region 28 and therefore do not substantially interfere with the treatment of the vascular condition. When the vascular condition has been satisfactorily treated, balloon 26 may be deflated. Balloon catheter 20 then may be retracted proximally into the confines of outer sheath 62, which may disposed coaxially over outer shaft member 22, as shown in FIG. 1A.

As balloon 26 is retracted into outer sheath 62, tapered proximal regions 42 of folding members 40 may engage outer sheath 62. Due to the configuration of folding members 40 and biasing members 47, further retraction of balloon 26 into outer sheath 62 will cause balloon 26 to contract and fold in a more orderly, counter-clockwise fashion. Therefore, by using folding members 40 in conjunction with balloon 26, a reduced cross-sectional balloon profile may be achieved in the deflated state, as opposed to balloons that may not collapse completely and may be difficult to retrieve.

Figure 2B:
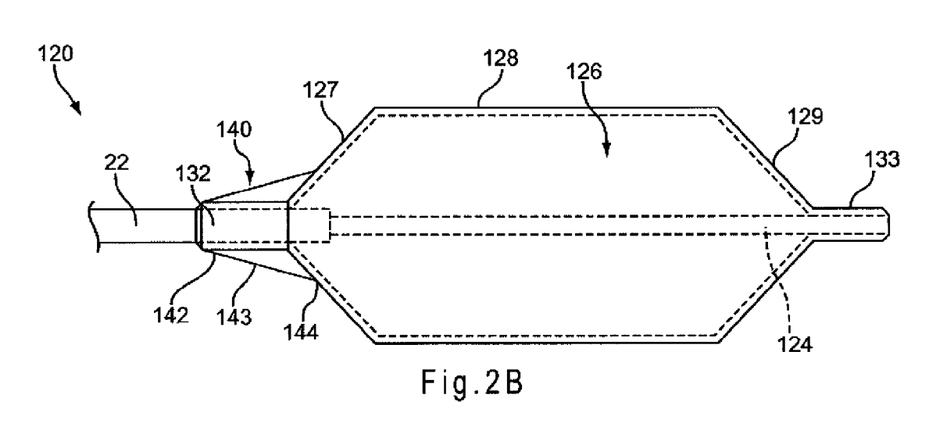

Referring now to FIGS. 2A-2B, an alternative embodiment of a balloon catheter is provided. In FIGS. 2A-2B, balloon catheter 120 is similar to balloon catheter 20 of FIGS. 1A-1B, with a main exception that four folding members 140 are provided, each having proximal end 142, distal end 144, and tapered central portion 143 extending therebetween. Central portion 143 extends directly between proximal attachment region 132 and proximal taper 127 of balloon 126, as shown in FIG. 2A.

Like folding members 40 described above, folding members 140 may be integrally formed with balloon 126, such that proximal taper 127 of balloon 126 transitions into central portion 143. Alternatively, if manufactured separately, folding members 140 may be attached between proximal attachment region 132 and proximal taper 127 of balloon 126, e.g., via adhesive or other suitable means. Further, as noted above, one or more biasing members 47 may be disposed between folding members 140 and an adjacent portion of balloon 126 to facilitate folding of the balloon in a more orderly fashion.

An exemplary method of operation of balloon catheter 120 is similar to the operation of balloon catheter 20, as explained in FIGS. 1A-1B above. When the vascular condition has been satisfactorily treated, balloon 126 may be deflated, and balloon catheter 120 then may be retracted proximally into the confines of an outer sheath, such as outer sheath 62 of FIG. 1A. As balloon 126 is retracted into the outer sheath, central regions 143 of folding members 140 may engage the outer sheath. Due to the configuration of folding members 140, and optionally biasing members 47, further retraction of balloon 126 into the outer sheath will cause balloon 126 to contract and fold in a more orderly fashion. By enhancing the folding capability of balloon 126, the overall cross-sectional profile of balloon 126 may be reduced when deflated.

It should be noted that, in the embodiments of FIGS. 1-2 above, if two folding members are provided at opposing locations, i.e., substantially 180 degrees apart, then the folding members may further facilitate removal of the balloon by expanding the outer sheath. In particular, the provision of two oppositely disposed folding members may cause the outer sheath to expand in one radial direction, before having to expand in all radial directions to accept the deflated balloon. This allows the outer sheath to begin expanding earlier during balloon catheter removal, which may reduce the force required to retract the balloon into the confines of the outer sheath. Alternatively, retraction of the balloon into the outer sheath may pre-collapse the taper of the balloon.

Figure 3A:
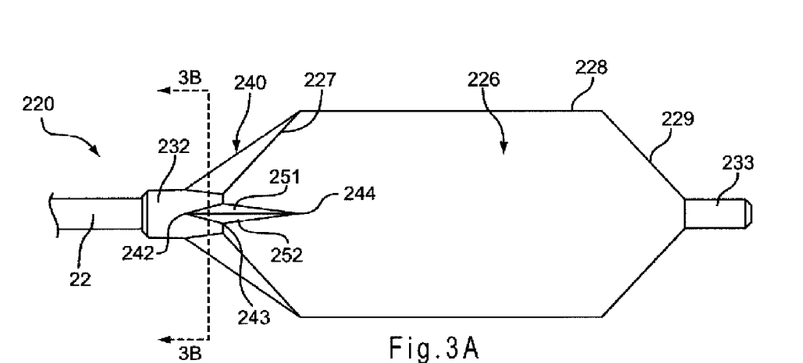
FIGS. 3A-3B are, respectively, a side view of a third embodiment and a cross-sectional view along line 3B-3B of FIG. 3A.
Figure 3B:
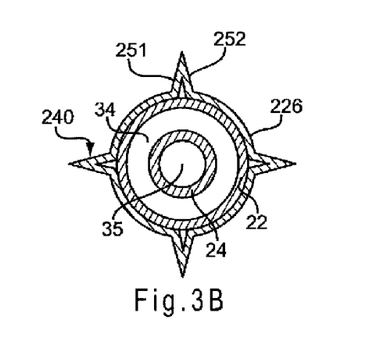

Referring now to FIGS. 3A-3B, a further alternative embodiment of a balloon catheter is provided. In FIGS. 3A-3B, folding members 240 comprise a fluted configuration. Specifically, each folding member 240 is formed in a radially outward direction and comprises proximal end 242, distal end 244, and central portion 243 formed therebetween. There is a proximal taper between proximal end 242 and central portion 243, and a distal taper between central portion 243 and distal end 244, as shown in FIG. 3A. Due to their fluted configurations, folding members 240 comprise opposing triangular-shaped sides 251 and 252, as shown in FIG. 3A. As shown in FIG. 3B, when viewed from a cross-sectional profile, opposing sides 251 and 252 form a substantially V-shaped configuration.

Like folding members 40 described above, folding members 240 may be integrally formed with balloon 226, such that proximal taper 227 of balloon 226 transitions into folding member 240. Alternatively, if manufactured separately, folding member 240 may be attached between proximal attachment region 232 and proximal taper 227 of balloon 226, e.g., via adhesive or other suitable means. Further, as noted above, one or more biasing members 47 may be disposed between folding members 240 and an adjacent portion of balloon 226 to facilitate folding of balloon 226 in a more orderly fashion.

An exemplary method of operation of balloon catheter 220 is similar to operation of balloon catheter 20, as explained in FIGS. 1A-1B above. When the vascular condition has been satisfactorily treated, balloon 226 may be deflated, and balloon catheter 220 then may be retracted proximally into the confines of an outer sheath, such as outer sheath 62 of FIG. 1A. As balloon 226 is retracted into the outer sheath, opposing sides 251 and 252 of folding members 240 may engage the outer sheath. As explained above, due to configuration of folding members 240, and optionally biasing members 47, further retraction of balloon 226 into the outer sheath will cause balloon 226 to contract and fold in a more orderly fashion.

In one exemplary method of manufacture, a laser may be used to bond proximal attachment region 232 of balloon 226 to outer shaft member 22. The pattern of bonding may be varied by varying the axial speed of the laser, the rotational speed of outer shaft member 22, and/or by modulating the laser beam. Such manufacturing techniques may be useful for bonding proximal attachment region 232 to outer shaft member 22, while avoiding bonding the proximal portions of fluted-shaped folding members 240.

Figure 4:
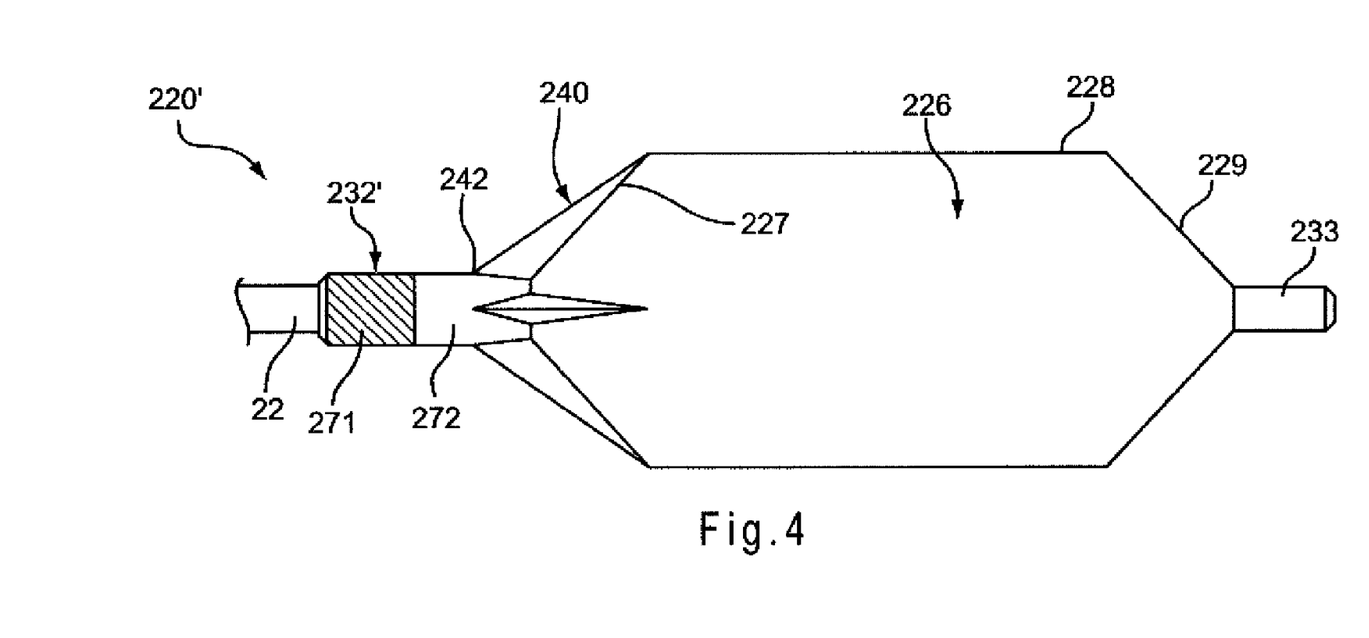
FIG. 4 is an alternative embodiment of FIG. 3A in which an unbonded balloon region is employed.

Referring now to FIG. 4, an alternative embodiment of the balloon catheter of FIGS. 3A-3B is described. Balloon catheter 220' of FIG. 4 is similar to balloon catheter 220, with the main exception that proximal attachment region 232' comprises bonded region 271 and unbonded region 272. While region 271 of balloon 226 is bonded to outer shaft member 22, region 272 is not bonded to reduce or eliminate peel-away stresses that may be imposed upon fluted folding members 240. In particular, by providing unbonded zone 272 just proximal to folding members 240, and in the spaces between folding members 240, the proximal ends 242 of folding members 240 are more likely to maintain their desired fluted configurations.

Figure 5A:
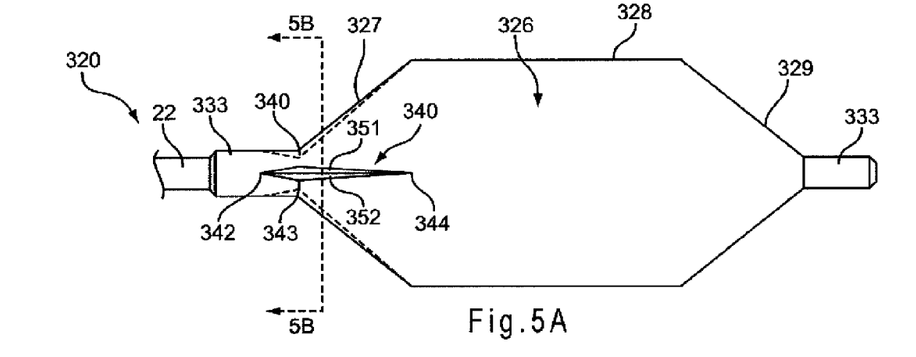
FIGS. 5A-5B are, respectively, a side view of a further alternative embodiment and a cross-sectional view along line 5B-5B of FIG. 5A.
Figure 5B:
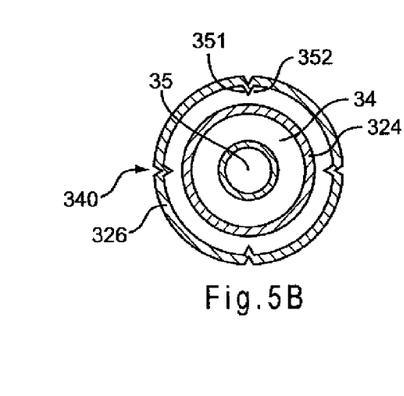

Referring now to FIGS. 5A-5B, a further alternative embodiment of a balloon catheter is provided. Folding members 340 are integrally formed with balloon 326 and may extend from proximal attachment region 333 into proximal taper 327 of balloon 326, as shown in FIG. 5A. In this embodiment, folding members 340 comprise internal grooves having an inverted fluted configuration. Specifically, each folding member 340 is formed in a radially-inward direction, as compared to the radially-outward direction of folding members 240 above. Folding members 340 comprise proximal end 342, distal end 344, and central portion 343 formed therebetween. There is a proximal taper between proximal end 342 and central portion 343, and a distal taper between central portion 343 and distal end 344, as shown in FIG. 5A. Moreover, due to their fluted configurations, folding members 340 comprise opposing triangular-shaped sides 351 and 352, as shown in FIG. 5A. When viewed from a cross-sectional profile, the opposing sides 351 and 352 form a substantially V-shaped configuration, as shown in FIG. 5B.

An exemplary method of operation of balloon catheter 320 is similar to operation of balloon catheter 20, as explained in FIGS. 1A-1B above. When the vascular condition has been satisfactorily treated, balloon 326 may be deflated, and balloon catheter 320 then may be retracted proximally into the confines of an outer sheath, such as outer sheath 62 of FIG. 1A. As balloon 326 is retracted into the outer sheath and proximal tapered region 327 contacts the outer sheath, folding members 340 act as folding points for balloon 326. In effect, further retraction of balloon 326 into the outer sheath will cause balloon 326 to contract and fold in a more orderly fashion.

Figure 6:
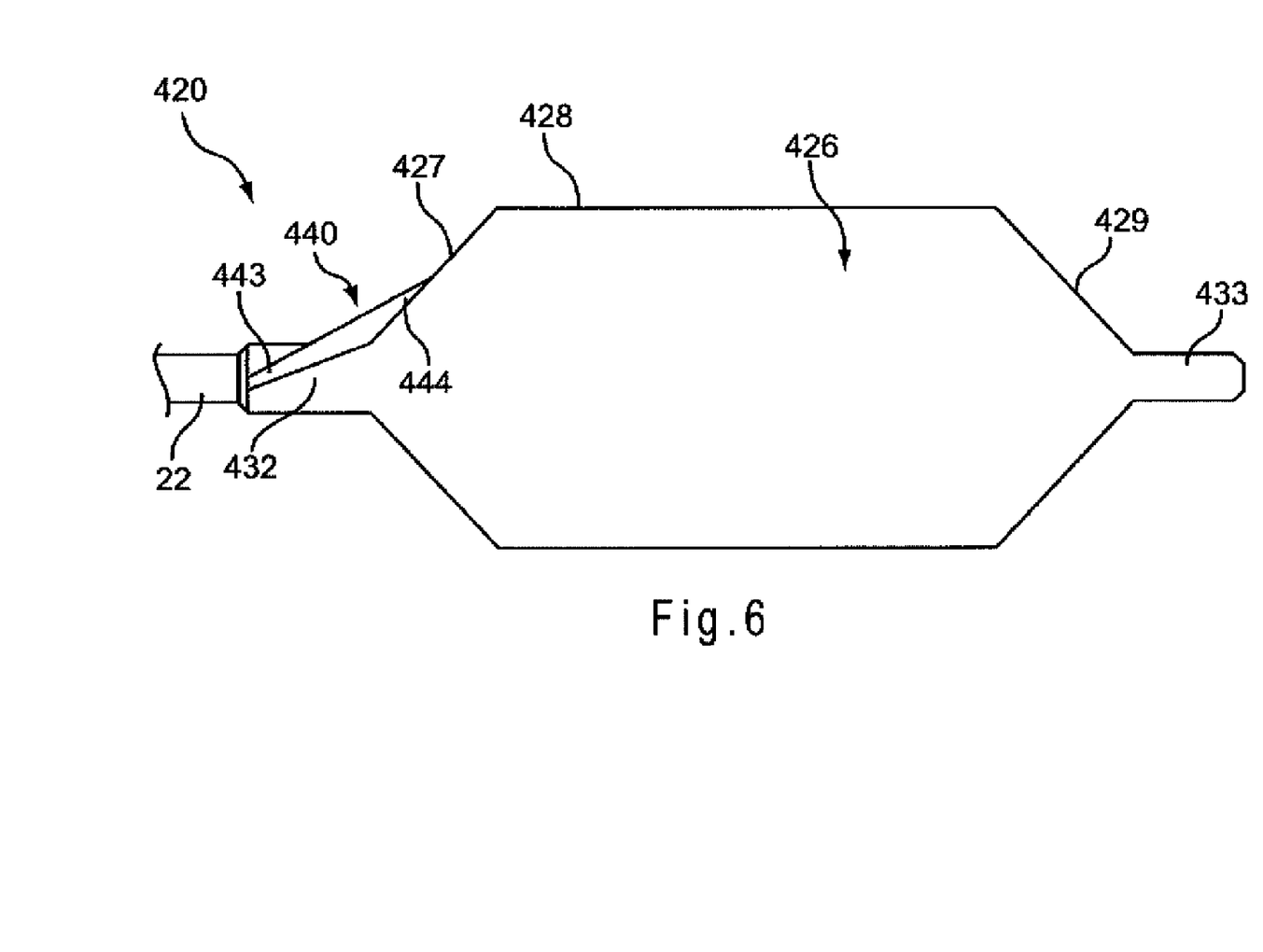
FIG. 6 is a side view of a further alternative embodiment of a balloon having at least one folding member.

Referring now to FIG. 6, an alternative embodiment of a balloon catheter is provided. In FIG. 6, balloon catheter 420 is similar to balloon catheter 20 of FIGS. 1A-1B, with a main exception that at least one curved or spiral-shaped folding member 440 having proximal end 443 and distal end 444 is provided. Proximal end 443 is attached to proximal attachment region 432 of balloon 426, while distal end 444 is attached to proximal taper 427 of balloon 426 at a location circumferentially offset from proximal end 443. By having proximal and distal ends 443 and 444 circumferentially offset from one another to obtain a curved or spiral shape, folding member 440 and balloon 426 may fold in a more orderly fashion.

As depicted in FIG. 6, proximal end 443 of folding member 440 is attached to proximal attachment region 432 and then extends approximately 90 degrees in a counter-clockwise direction before distal end 444 is attached to proximal taper 427. Although a 90 degree circumferential offset is depicted, proximal and distal ends 443 and 444 of folding member 440 may be offset a greater or lesser amount.

Moreover, a portion of folding member 440 extending between proximal and distal ends 443 and 444 may be straight, convexly curved, and so forth. Further, while one spiral-shaped folding member 440 is depicted, it will be apparent that a greater number may be disposed about the circumference of proximal attachment region 432 and/or proximal taper 427.

Like folding members 40 described above, folding member 440 may be integrally formed with balloon 426, such that proximal taper 427 of balloon 426 transitions into distal end 444. Alternatively, if manufactured separately, folding member 440 may be attached between proximal attachment region 432 and proximal taper 427 of balloon 426, e.g., via adhesive or other suitable means. Further, as noted above, one or more biasing members 47 may be disposed between folding members 440 and an adjacent portion of balloon 426 to facilitate folding of the balloon in a more orderly fashion.

An exemplary method of operation of balloon catheter 420 is similar to the operation of balloon catheter 20, as explained in FIGS. 1A-1B above. When the vascular condition has been satisfactorily treated, balloon 426 may be deflated, and balloon catheter 420 then may be retracted proximally into the confines of an outer sheath, such as outer sheath 62 of FIG. 1A. As balloon 426 is retracted into the outer sheath, folding members 440 may engage the outer sheath. Due to the configuration of folding members 440, and optionally biasing members 47, further retraction of balloon 426 into the outer sheath will cause balloon 426 to contract and fold in a more orderly fashion. By enhancing the folding capability of balloon 426, the overall cross-sectional profile of balloon 426 may be reduced when deflated.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An apparatus suitable for facilitating folding of a balloon before, during or after a medical procedure, the apparatus comprising:
    at least one catheter shaft member comprising proximal and distal ends;
    a balloon comprising a proximal taper, a distal taper, and a central region formed therebetween, wherein the balloon is coupled to the catheter shaft member;
    at least one folding member disposed along at least a portion of the proximal taper of the balloon, wherein the folding member terminates proximal to the central region of the balloon,
    wherein the folding member comprises at least one radially-projecting member having a proximal tapered region, a central region, and a distal tapered region; and
    at least one biasing member disposed between the folding member and an adjacent portion of the balloon to promote folding of the balloon in a clockwise or counter-clockwise direction.

2. The apparatus of claim 1 wherein the folding member is integrally formed with the balloon.

3. The apparatus of claim 1 wherein the central region of the balloon is configured to perform angioplasty on an inner wall of a vessel.

4. The apparatus of claim 1 wherein the folding member comprises a proximal end, a distal end, and a central region formed therebetween, wherein the balloon is unbonded to the catheter shaft member at a location proximal to the proximal end of the folding member.

5. Apparatus suitable for facilitating folding of a balloon before, during or after a medical procedure, the apparatus comprising:
    at least one catheter shaft member having proximal and distal ends;

a balloon having a proximal and distal regions, wherein the balloon is coupled to the catheter shaft member;

at least one folding member disposed along a portion of the proximal region the balloon; and at least one biasing member disposed between the folding member and an adjacent portion of the balloon.

6. The apparatus of claim 5 wherein the biasing member comprises a heat bond formed between the folding member and the adjacent portion of the balloon.

7. The apparatus of claim 5 wherein the biasing member comprises a biocompatible adhesive disposed between the folding member and the adjacent portion of the balloon.

8. The apparatus of claim 5 wherein each one of the biasing members is coupled to a respective folding member, wherein each biasing member is disposed at a location counter-clockwise to each folding member to promote folding of the balloon in a counter-clockwise direction.

9. The apparatus of claim 5 wherein each one of the biasing members is coupled to a respective folding member, wherein each biasing member is disposed at a location clockwise to each folding member to promote folding of the balloon in a clockwise direction.

10. An apparatus suitable for facilitating folding of a balloon before, during or after a medical procedure, the apparatus comprising:

at least one catheter shaft member comprising proximal and distal ends;

a balloon having a proximal and distal regions, wherein the balloon is coupled to the catheter shaft member; and at least one folding member disposed along a portion of the proximal region the balloon, wherein the folding member projects radially outward relative to the catheter shaft member.

11. The apparatus of claim 10 wherein the folding member comprises at least one radially-projecting member comprising a fluted configuration.

12. The apparatus of claim 10 wherein the folding member comprises at least one radially-projecting member comprising a spiral-shaped configuration.

13. The apparatus of claim 10 wherein the folding member comprises at least one radially-projecting member having a proximal end, a distal end, and a tapered central portion extending therebetween.

14. The apparatus of claim 10 wherein the folding member comprises at least one radially-projecting member having a proximal tapered region, a central region, and a distal tapered region.

* * * * *